US009439619B1

(12) United States Patent
Nance et al.

(10) Patent No.: US 9,439,619 B1
(45) Date of Patent: Sep. 13, 2016

(54) TARGETING SYSTEM FOR USE WITH X-RAY MACHINES

(71) Applicants: Kirby Nance, Marine, IL (US); Karen Nance, Marine, IL (US)

(72) Inventors: Kirby Nance, Marine, IL (US); Karen Nance, Marine, IL (US)

( * ) Notice: Subject to any disclaimer, the term of this patent is extended or adjusted under 35 U.S.C. 154(b) by 46 days.

(21) Appl. No.: 14/688,268

(22) Filed: Apr. 16, 2015

(51) Int. Cl.
*A61B 6/00* (2006.01)
*A61B 6/08* (2006.01)

(52) U.S. Cl.
CPC *A61B 6/587* (2013.01); *A61B 6/08* (2013.01)

(58) Field of Classification Search
USPC .................................................. 378/206, 205
See application file for complete search history.

(56) References Cited

U.S. PATENT DOCUMENTS

| 5,283,808 | A | * | 2/1994 | Cramer | A61B 6/08 378/205 |
|---|---|---|---|---|---|
| 6,267,502 | B1 | | 7/2001 | McNeirney et al. | |
| 7,806,591 | B2 | | 10/2010 | Wang et al. | |
| 8,434,942 | B2 | | 5/2013 | Lenchig, Jr. | |
| 8,755,114 | B1 | | 6/2014 | Tanner et al. | |

* cited by examiner

*Primary Examiner* — Kiet T Nguyen
(74) *Attorney, Agent, or Firm* — Polster, Lieder, Woodruff & Lucchesi, LC

(57) ABSTRACT

Apparatus for use with a C-arm type x-ray unit (10) to locate and center an x-ray target area. The unit has an x-ray emitter (20) located at one end of a C-arm (50) and an x-ray receptor located at the other end of the C-arm. A ring-shaped band (45) adjustably fits around an outer end of the x-ray receptor. A first laser light source (90) and a second laser light source (100) are carried on the band in a predetermined orientation to each other. The laser light sources each project a fan shaped laser light into the target area between the x-ray emitter and the x-ray receptor. The beams are adjusted to determine a center of the target area through which x-rays are propagated when a patient is positioned in the x-ray unit for a procedure to be performed.

16 Claims, 6 Drawing Sheets

TARGETING SYSTEM FOR USE WITH X-RAY MACHINES

BACKGROUND OF THE INVENTION

This invention relates to x-ray positioning systems; and, more particularly, to a dual laser apparatus and method for aiming at and targeting the center of an x-ray field for subsequent use in performing medical diagnostics or procedures involving the use of an x-ray machine.

In setting up for a procedure involving x-rays, it is important to properly align the equipment so that when x-rays are directed at a patient's or subject's body by an x-ray machine, they are directed at the correct part of a person's anatomy. This prevents potentially harmful radiation for being directed at wrong parts of the person's body, or inadvertently at others who may be present for the procedure. There are a number of currently known procedures for affecting proper alignment, and while each may work to accomplish their goal, each has certain drawbacks.

In U.S. Pat. No. 6,267,502 to McNeirney, there is disclosed a device to assist alignment of an x-ray beam center to an image receptor center; after which the device is removed so the patient can be properly put in place for an x-ray procedure which is to be performed. The drawback with McNeirney is that the device must be removed before the patient is in place, and because of this, real-time information as to the location of the x-ray field's center cannot be known during the procedure and harm could result if the center shifts for some reason. In addition, McNierney also requires use of an opaque target which has to be positioned in the radiation field as part of the alignment process.

Next, U.S. Pat. No. 7,806,591 to Wang is directed to determining the positional alignment between a light beam and an x-ray beam, and vice versa. The device is for use on a non C-arm type fluoroscopy unit and employs two laser lights attached to an x-ray source. The lights are aimed at a reflective surface which is attached to, and located to one side of an image receptor. The receptor reflects the laser light back to the x-ray source with an operator then observing where light strikes the x-ray source so to determine if it is centered, or make appropriate adjustments to center it.

Among the drawbacks with the Wang device is that, during a procedure, the reflector is positioned below and to the side of the patient being x-rayed. If the patient is large, the reflector may be blocked from receiving the projected laser light. Further, the proximity of the reflector to the patient and x-ray technician is such that it can easily be dislodged or misaligned by the patient or technician. Also, use of the Wang device involves a significant amount of training before a technician can reliably set it up and use it. This includes having the technician constantly having to monitor two areas, the laser reflector, and the x-ray source.

U.S. Pat. No. 8,434,942 to Lenchig is directed at lighting apparatus for flooding light onto an area within an x-ray field of a non-portable C-arm fluoroscopy unit so to project a bright light into the area. The apparatus comprises a housing that surrounds an image receptor of an x-ray fluoroscope, and at least one light-emitting element installed within the housing and aimed downwards towards an x-ray source of the fluoroscope. The apparatus further employs up to three focusing mechanisms for focusing the light emitted. These fit over the light-emitting element, and a fastener for coupling the housing to an x-ray receiving element. A separate power supply unit, not coupled to the housing, provides electrical current to the light-emitting element.

Drawbacks of the apparatus are that it is designed for flooding light into a general area, not targeting a point; the large number of components an operator must install with respect to the optical elements; that the apparatus takes up space in the area below an image receptor, which area is for patient placement; that power to run the apparatus is routed through an electrical cord from a remote source; and, its non-portability.

U.S. Pat. No. 8,755,114 to Tanner describes a device for use with a binocular microscope for light illumination and uses a targeting light directed at a subject area. The device includes a control unit and a light source coupled with a targeting laser light to position a specimen in the microscope's field of view for examining the specimen. The device is ring-shaped and attached to the microscope using set screws. It is located below the magnifying objective lens and above the subject stage. Power to the device is by an electrical power cord connected between an external power source and the control unit. The control unit, which is located some distance from the ring shaped device, enables an operator to control light intensity. Connecting the components of the device and the control unit together, and their subsequent disengagement, is a time consuming process.

Other drawbacks of the device are that power is required from a remote source and a power cord is not supplied with the device; special tools are required for the device's assembly; the device is only for use with a microscope; when installed, the device attaches below the face of the microscope and invades the space designated for subject placement; the device requires multiple parts (e.g., control unit and power supply) not incorporated into a single unit; the device requires placement of a beam-splitter or mirror into the optical path of the microscope; the lasers used cannot be adjusted; and, the microscope does not involve radiation.

The current invention, as described hereinafter, overcomes the various drawbacks associated with this art, and has other advantages as well.

BRIEF SUMMARY OF THE INVENTION

The present invention is directed to apparatus incorporating two laser assemblies, a power supply and a latch assembly, all of which are installed on and carried by a band made of appropriate material such as aluminum. The band of aluminum is expandable by opening the latch assembly. Once unlatched, the band is wrapped about; i.e., encircles the receptor end of a C-arm x-ray system and then the latch assembly is reclosed to hold the laser aiming system solidly in place.

The laser light sources installed on the band are centered 90° from each other. When the power supply is activated, a visible fan shaped beam of coherent light is emitted from each of the two laser assemblies. Because of the 90° displacement of the laser assemblies, the two fan-shaped beams cross each other to form an easily viewable target area. The laser assemblies are covered with a housing having two openings: 1) an opening through which the laser beam's coherent light is emitted, and 2) an opening for accessing a control arm to adjust the aim of the laser beam. The control arm at the side of a housing is maneuverable by an operator to fine tune the laser aiming system so to locate the exact center of an x-ray emitter field.

An advantage of the present invention is to provide an alignment of a preferred x-ray target view without inadvertently exposing physicians, assistants and patients to the detrimental effects of radiation. The visible laser light beam is easily adjusted and its focus is held precisely in place. The highly visible target light generated by the apparatus has an added advantage of being discernible at a low threshold distance of less than 3½" from a receptor upon which it impinges.

Another significant advantage of the present invention is that it is extremely useful in the set-up for pain management procedures with commonly used C-arm devices.

Other objects and features will be in part apparent and in part pointed out hereinafter.

BRIEF DESCRIPTION OF THE SEVERAL VIEWS OF THE DRAWINGS

The accompanying figures, together with detailed description which follows, form part of the specification and illustrate the various embodiments described in the specification.

Corresponding reference characters indicate corresponding parts throughout the several views of the drawings.

DETAILED DESCRIPTION OF INVENTION

The following detailed description illustrates the invention by way of example and not by way of limitation. This description clearly enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

Referring to the drawings, the present invention is directed to a laser aiming system for use in designating a target area at the center of an invisible x-ray beam as propagated by a C-arm x-ray unit or machine. The system or apparatus is totally contained around an x-ray receptor so as not to block or impede any radiation from reaching the receptor. The system and its apparatus enables an x-ray beam target to be precisely known to persons using the C-arm x-ray machine without any detrimental radiation exposure. Accordingly, personnel associated with a procedure involving the x-ray machine; i.e., physicians, lab assistants, and the patients, have their chances of radiation exposure significantly minimized during a procedure.

Figure 1:
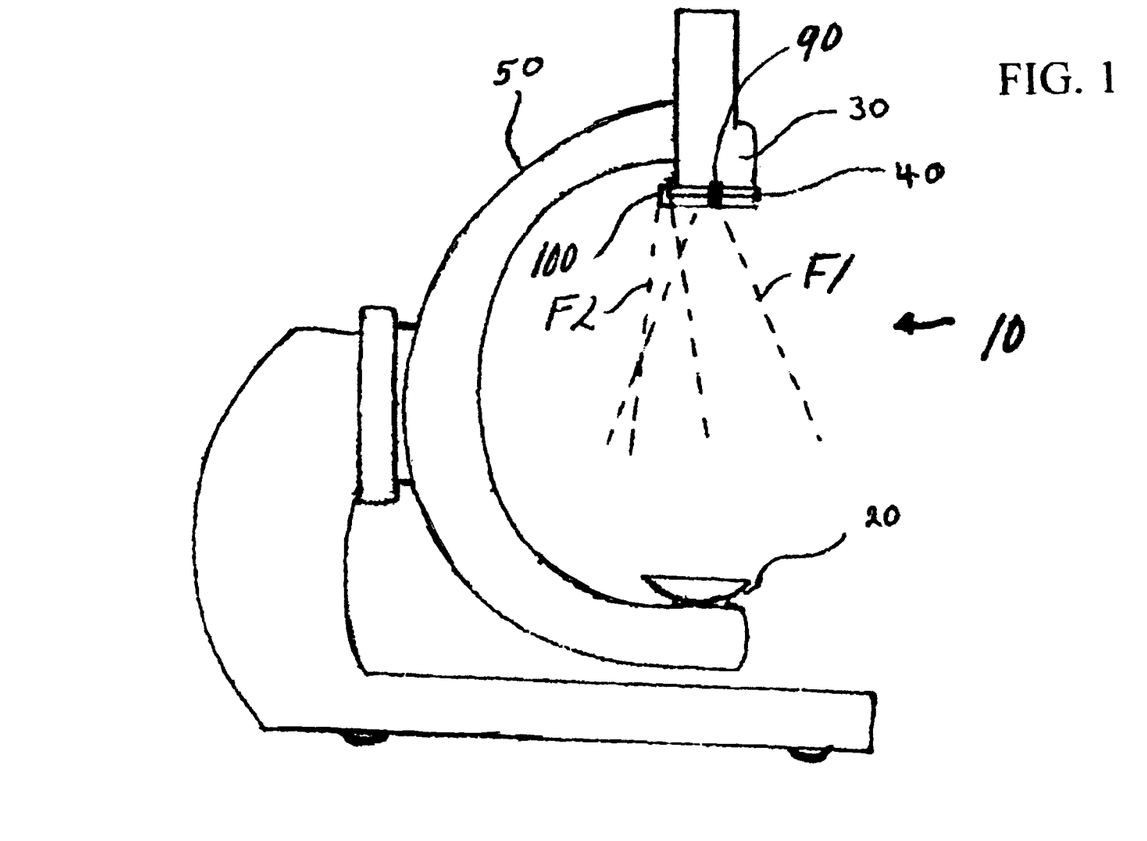
FIG. 1 illustrates a C-arm type x-ray unit with the laser aiming system of the present invention mounted around an x-ray receptor of the unit.

Referring to FIG. 1, a C-arm x-ray machine 10 has a C-arm 50. Such machines are well-known in the art and their design and construction are not described. X-ray machine 10 has an x-ray emitter 20 located at the lower end of arm 50. Emitter 20 generates an x-ray field which is directed upwardly toward an x-ray receptor 30 located at the opposite, upper end of arm 50. A laser aiming system of the present invention is indicated generally 40 in FIG. 1. As shown in the Fig., assembly 40 is attached to x-ray receptor 30.

During an x-ray procedure, a patient is positioned between x-ray emitter 20 and x-ray receptor 30. Because patients differ in size, their particular mass to be x-rayed will be either closer to, or farther from, x-ray receptor 30, depending on their size. Also, it is known that the attending physician can exercise a preference for specific patient placement in relation to x-ray receptor 30, and this may place a patient closer to, or farther away from, the receptor. Laser aiming system 40 allows for exemplary use and a readable target depiction at the distance of less than 3½" distance from receptor 30.

Figure 3:
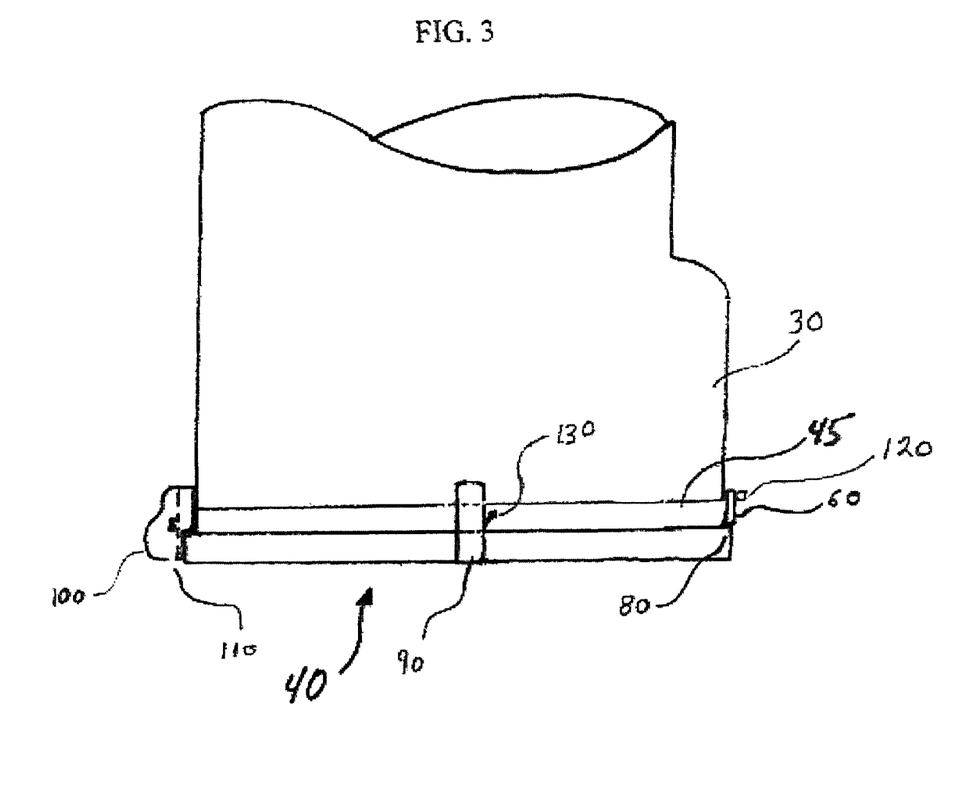
FIG. 3 illustrates an upper end of the C-arm to which a band of the laser aiming system is mounted.

Referring to FIG. 3, laser aiming system 40 is shown attached to x-ray receptor 30. It will be understood by those skilled in the art that the body circumference of x-ray receptor 30 will differ from its face's circumference. This difference in circumference is represented by the lip or edge 80 at the x-ray receptor's face. This lip or edge 80 has a larger circumference than that of the body of x-ray receptor 30. Assembly 40 of the present invention contacts this lip or edge 80, along with contacting the body of receptor body, and the assembly is held in place by this dual contact.

Figure 2:
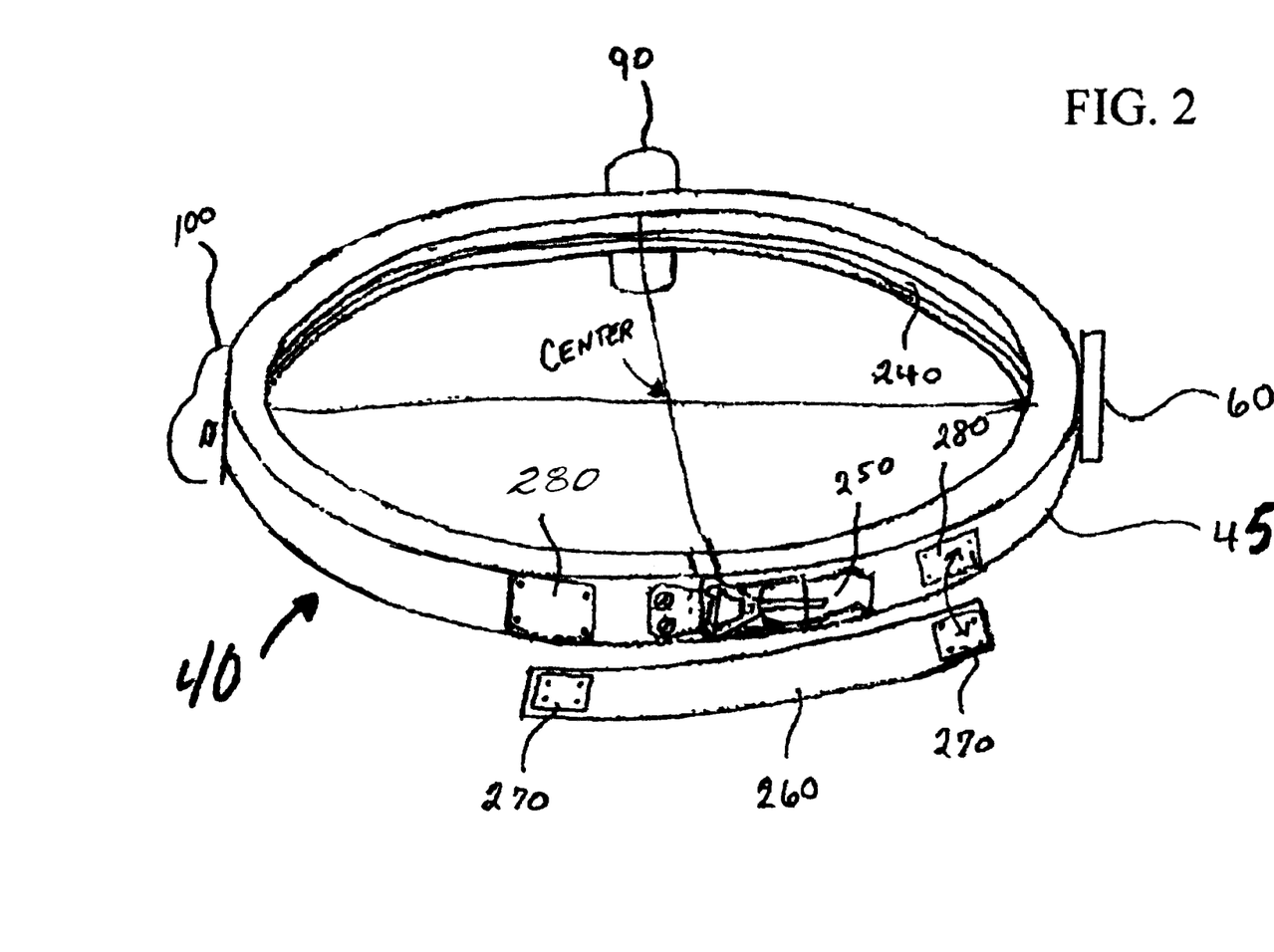
FIG. 2 is a perspective view of the laser aiming system.

Referring to FIGS. 2 and 3, laser aiming assembly 40 includes a power supply 60, a first laser assembly housing 90 housing a first laser light source, a second laser assembly housing 100 housing a second laser light source, and a band 45. The two laser assembly housing components, 90 and 100 are identical to each other and are preferably installed 90° apart from each other on band 45 (see particularly FIG. 2); although in other embodiments, the housings and their respective light sources can be positioned on band 45 between 60° and 120° apart from each other. These housing components, together with power supply 60, are attached to band 45 and fixed through the band with stainless steel screws whose threads are coated with a lock-tight type material to ensure stability. Further, power supply 60 is movable about band 45 so to be in a convenient location relative to the location of housings 90 and 100. In addition, the inner face of the band may be fitted with a cushioning material so as not to damage x-ray receptor 30 when mounted on or to the receptor.

Figure 6:
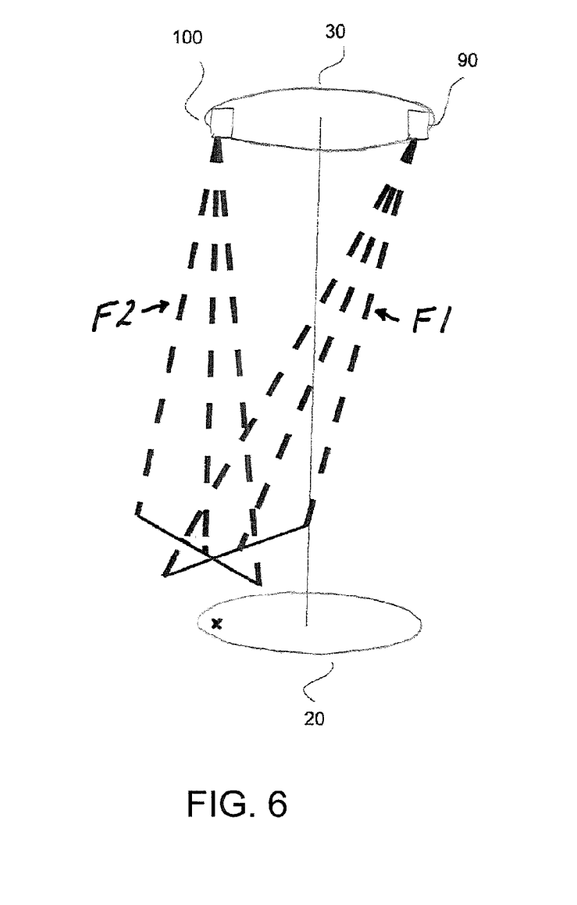
Figure 7:
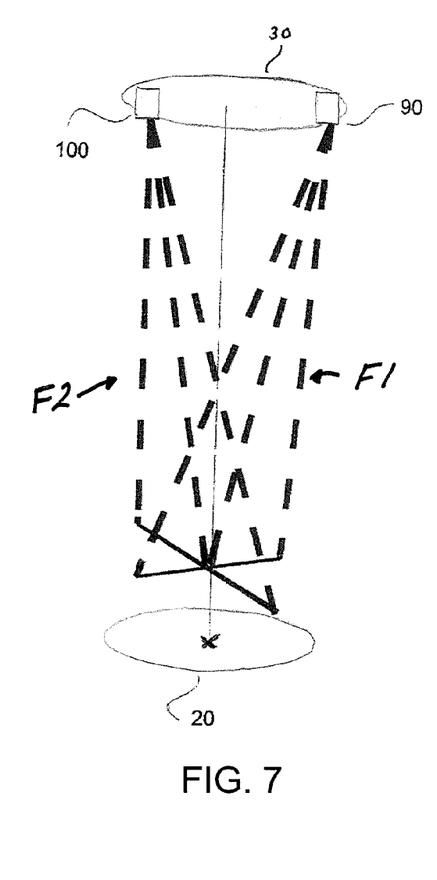

Each laser light source emits a fan shaped beam of laser light respectively indicated F1 and generated by the first laser light source installed in housing 90, and F2, generated by the second laser light source installed in housing 100. These beams are shown in FIGS. 1, 6 and 7, and are adjusted to ascertain the center of the x-ray pattern emitted by x-ray emitter 20 toward x-ray receptor 30 during a patient procedure.

Next, a laser control arm 130 (see FIG. 4) is located to the side of laser assembly housings 90 and 100. Control arm 130 is accessible on the outer side of each of the two laser assembly housings 90 and 100. Laser control arm 130 comprises a rod threaded at its end inside the laser assembly housings, and has an ergonomic cap at its opposite, outer and accessible end. The laser control arm 130 has two functions: 1) to allow x-ray technicians or a physician to align a visible laser light to the center of the C-arm's x-ray field, and 2) to set or fix the visible laser light at a preferred position.

As further shown in FIG. 3, housing 100 has an opening 110 forming an aperture by which a laser beam is directed at x-ray emitter 20. Housing 90 has a similar opening (not shown in FIG. 3) for also directing emitted laser beam light at emitter 20. Power supply 60 is connected to, and supplies power to, both laser assemblies 90 and 100. Power to each housing assembly is through a push-button switch located on power supply 60. Switch 120 is a push-button type switch that allows the laser assemblies installed in housings 90 and 100 to be energized or de-energized at the same time. Although not shown, a timer is available to be used with the switch to automatically turn OFF the apparatus once the alignment procedure is complete.

Figure 4:
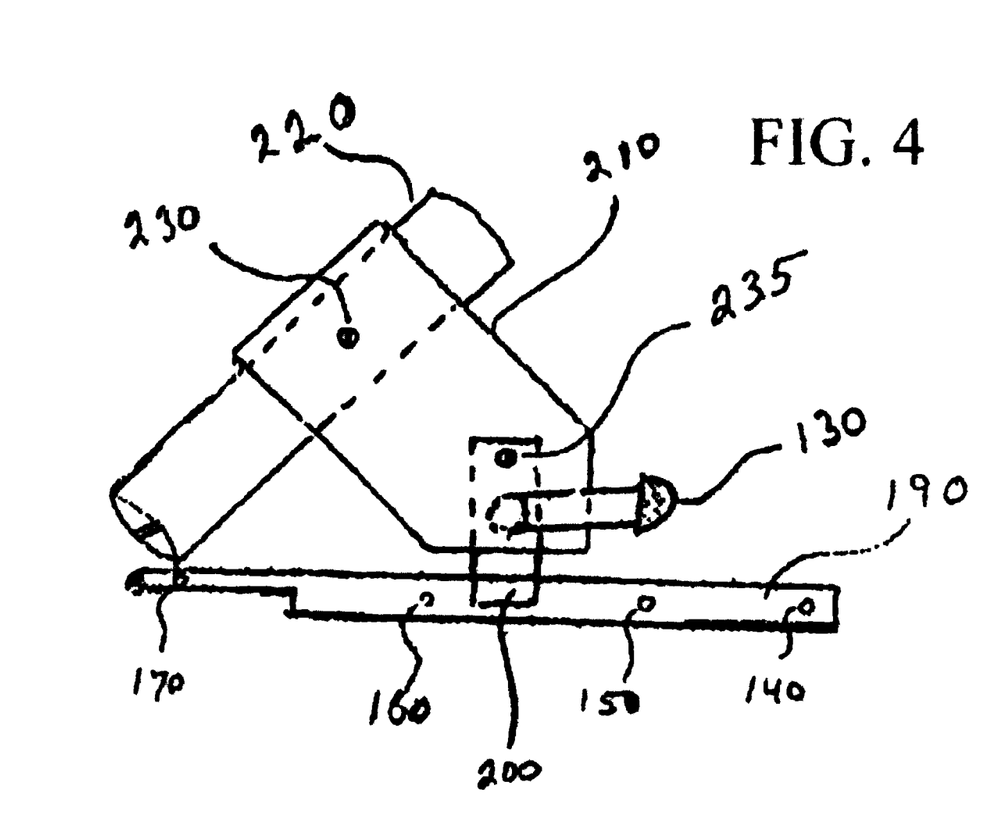
FIG. 4 is a view of the laser aiming systems assembly and controls.
Figure 5:
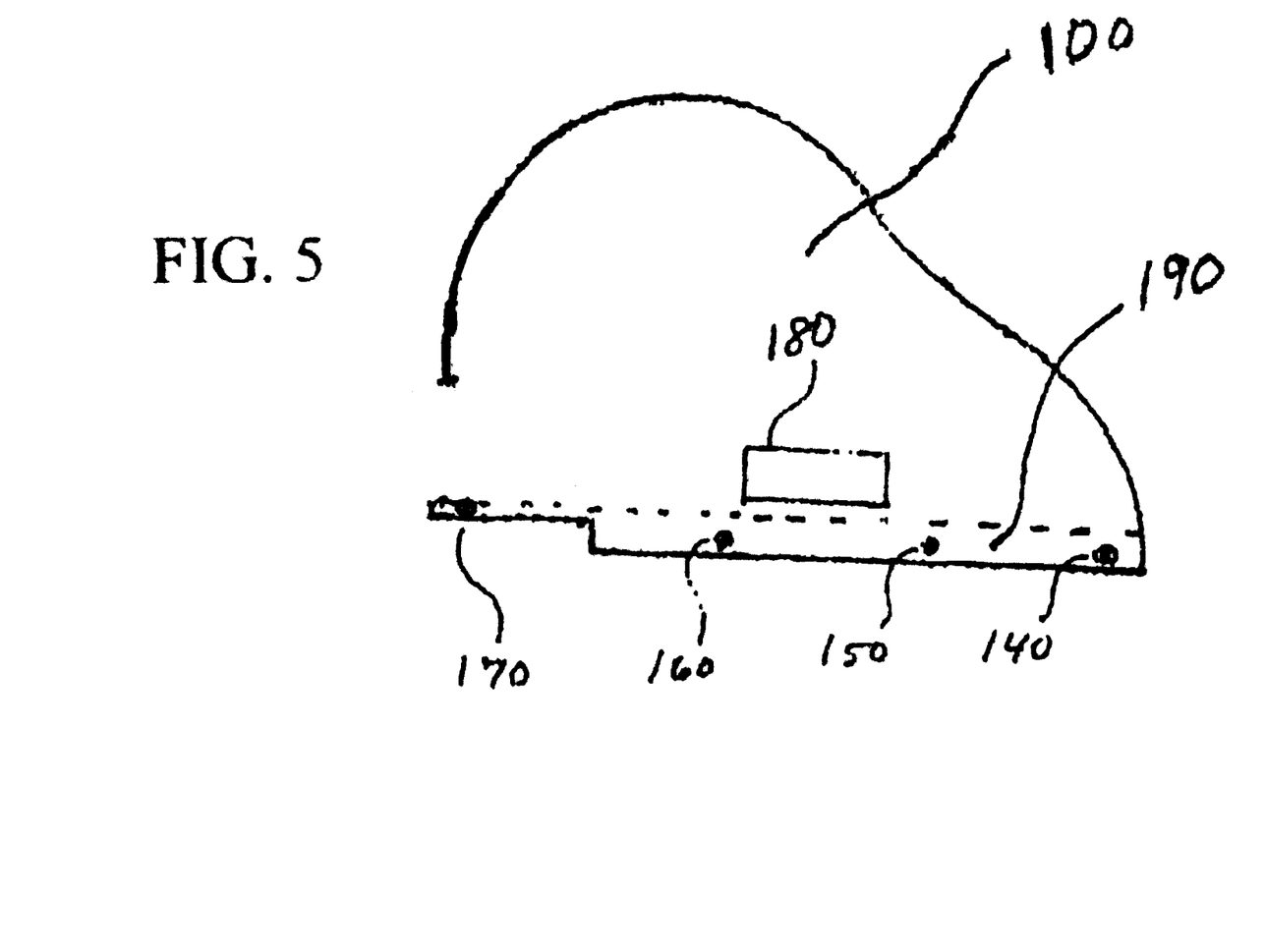
FIG. 5 illustrates a housing cover of the laser assembly of the aiming system; and, FIGS. 6 and 7 illustrate the fan shaped laser light beams of the system and their adjustment to locate the center of a field generated by an x-ray emitter of the C-arm unit.

Referring to FIGS. 4 and 5, laser assembly housing 100 is secured to a base laser plate 190 by stainless screws 140, 150, 160 and 170. These are replicated on laser assembly housing 90. Located on one side of laser assembly housings 90 and 100 is a control arm opening 180 through which laser control arm 130 extends. The elements installed in housings 90 and 100 are attached to laser plate 190 by means of a rotation post 200. Laser plate 190 has a concave curved surface which conforms to the curvature of the C-arm of the x-ray machine's receptor end. Rotation post 200 supports a laser block 210 that envelopes and supports a laser emitter 220 which emits visible laser light to a target field located between x-ray emitter 20 and x-ray receptor 30.

Laser control arm 130 extends into a side of laser block 210 and through the laser block for adjustable contact with rotation post 200. This adjustable contact is achievable because laser control arm 130 has the threaded end, and laser block 210 has a threaded bore into which this threaded end fits for making adjustments. The other end of laser control arm 130 extends away from laser block 210 and, as noted, has an ergonomic cap end.

Laser control arm 130 has multiple purposes. One is to make precision adjustments to the aim of laser emitter 220 at the target in the center of the x-ray field (see FIG. 2). These adjustments are necessary because all x-ray machines, including C-arm x-ray machines, are not routinely maintained in a factory condition. This includes the x-ray emitter 20, and this effects the radiation field which, during a procedure using the machine, needs to be accurately aimed at the precise center of x-ray receptor 30.

Adjustment of laser emitter 220 is accomplished by using laser control arm 130 to manipulate the emitter forward or back as necessary (left and right in FIG. 4). This, in turn, pivots laser block 210 and adjusts the aim of laser emitter 220. This adjustment of laser emitter 220 is reflected in an adjustment of the aim or target area of the laser light. It will be understood that there is also a laser control arm (not shown) located on the other laser assembly housing.

Referring to FIGS. 6 and 7, the fan shaped beams F1, F2 are visible beams of light produced by the laser emitters 220 respectively installed in housings 90 and 100. In FIG. 6, these beams are adjusted to an off-center position on the x-ray field produced by x-ray emitter 20. Using the adjustment features described above, in FIG. 7, the light beams F1, F2 are shown adjusted to a center position on the emitted x-ray field.

Another purpose of laser control arm 130 is that it can be adjusted or tightened against rotation post 200, which secures laser block 210, and therefore laser emitter 220, in a fixed position once the visible laser light beams are centered. This tightening is accomplished by turning threaded control arm 130. Upon achieving an acceptable aiming alignment using laser control arm 130, the threaded end of the control arm is twisted (in a clockwise direction) which brings it into contact with the rod of rotation post 200. This stops any further movement of laser block 210 and adjustment of the light emitted by laser emitter 220. Ease of rotation of laser control arm 130 is facilitated by its ergonomic cap end which provides for a comfortable and positive finger grip.

As also shown in FIG. 4, and pertaining to laser emitter 220, is a means for securing laser emitter 220 in laser block 210. This is accomplished using a set screw 230 which is located on, and threaded through, laser block 210 to lock everything in place by abutting it against the body of laser emitter 220. This locking action secures laser emitter 220 against any movement within laser block 210. Any subsequent adjustments necessary are made by loosening laser control arm 130, repositioning laser block 210 by an appropriate rotation, and then re-tightening laser control arm 130 back into a fixed position contacting rotation post 200. Laser control arm 130 then abuts against rotation post 200, arresting unwarranted movement of laser block 210, laser emitter 220 and it's illuminated target laser light.

In another embodiment of the invention, a pre-loaded spring is located between set screw 235 and rotation post 200 so to apply a continuous pressure which will hold laser block 210 in a desired position without having to tighten control arm 130.

Pertaining to rotation post 200, it is connected to plate 190 in such a manner as to arrest any movement of rotation post 200. This connection is at the bottom end of rotation post 200 and involves press fitting, use of a bonding material or other procedures which reach the same end result of no movement of the rotation post. Near the top of rotation post 200, a channel is cut around the circumference of the rotation post. A second set screw 235 is fitted into this channel and this fit facilitates a redundancy safety measure by arresting any upward movement of laser block 210 and attached components.

Laser aiming system band 40 has a spherical shape corresponding to the circumference of a C-arm 50s x-ray receptor 30. On an interior section of band 40 is an embedded channel which carries an electric wire 240 from power supply 60 to each laser assembly housing components, 90 and 100 so to power the laser assemblies.

A fastening latch 250 is used to expand band 40 so it can be installed on the circumference of a C-arm style x-ray machine's receptor 30 outer end. Fastening latch 250 is adjusted to tighten and secure band 40 to receptor 30. Fastening latch 250 is made of a stainless steel. A clasp is attached to one side of fastening latch 250 and attached to band 40 via screws, and a hook or curved fastener is attached to band 40 on the opposite side of the latch. These work together to latch the band to the outer end of x-ray receptor 30.

A strap 260 is installed as a redundancy safety feature on the band 40 near the fastening latch 250. Strap 260 is fitted over fastening latch 250, as shown in FIG. 2, and remains in place until access to fastening latch 250 is required. Strap 260 is a hook and loop fastener affixed to each end of strap 260. Strap 260 is fixed in place by a hook 270 and a loop 280 being joined by the user so to protect the fastening latch 250 from any accidental mishandling or unscheduled latch release.

The present invention is not limited to each specifically described measure but rather refers to any embodiments within the spirit and scope of the present invention which arrive at the same end achievement.

In view of the above, it will be seen that the several objects and advantages of the present disclosure have been achieved and other advantageous results have been obtained.

Having thus described the invention, what is claimed and desired to be secured by Letters Patent is:

1. Apparatus for use with a C-arm type x-ray unit to locate and center an x-ray target area, the x-ray unit having an x-ray emitter located at one end of a C-arm and an x-ray receptor located at the other end of the C-arm, comprising:
   a ring-shaped band adjustably fitting around an outer end of the x-ray receptor; and,
   a first laser light source and a second laser light source, said laser light sources being carried on the band in a predetermined orientation to each other, and the laser light sources each projecting laser light into the target area between the x-ray emitter and the x-ray receptor so to determine a center of the target area through which x-rays will be propagated when a patient is positioned in the x-ray unit for a procedure to be performed on the patient.

2. The apparatus of claim 1 further including a power source installed on the ring-shaped band for powering the laser light sources.

3. The apparatus of claim 2 wherein the location of the power source on the band is adjustable.

4. The apparatus of claim 2 in which the power source includes a switch controlling the supply of power to said first and second laser light sources.

5. The apparatus of claim 4 further including a timer for automatic shut-off of the apparatus.

6. The apparatus of claim 1 wherein said first laser light source and said second laser light sources are located circumferentially about the band 90° apart from each other.

7. The apparatus of claim 6 wherein each of said laser light sources generate a fan-shaped beam, the fan shaped beams intersecting at a center of the target area.

8. The apparatus of claim 7 in which both laser light beams are directed at the x-ray emitter.

9. The apparatus of claim 6 in which said first and second laser light sources are positioned between 60°-120° apart on the band.

10. The apparatus of claim 9 further including a latch mechanism for mounting the band on the x-ray receptor.

11. The apparatus of claim 9 wherein the inside of the band includes a cushioning material to prevent damage to the x-ray receptor when the band is installed.

12. The apparatus of claim 1 in which said first and second laser light sources are each enclosed in a separate housing installed on the band.

13. The apparatus of claim 12 further including an optional, a reflective material interposed between each laser and an aperture of the housing for the laser with the laser beams being reflected off the reflective material.

14. The apparatus of claim 13 further including a control arm installed in each housing to adjust the direction of the laser beam emitted by the laser light source installed in a housing.

15. The apparatus of claim 14 further including a post installed in each housing, the control arm installed in a housing being affixed to the post once the center of the x-ray field is located so to prevent inadvertent distortion of the center alignment.

16. The apparatus of claim 1 wherein said first and second light sources each emit a fan-shaped laser light beam for determining the center of the x-ray radiation to be projected by the x-ray emitter to the x-ray receptor.

* * * * *